United States Patent [19]

Madison et al.

[11] Patent Number: 4,985,561
[45] Date of Patent: Jan. 15, 1991

[54] SULFUR TRIOXIDE SULFONATION OF AROMATIC CHLOROFORMATES

[75] Inventors: Stephen A. Madison; Leonora M. Ilardi, both of Valley Cottage, N.Y.; Hans Cerfontain, Amsterdam, Netherlands

[73] Assignee: Lever Brothers Company, Division of Conopco, Inc., New York, N.Y.

[21] Appl. No.: 400,195

[22] Filed: Aug. 29, 1989

[51] Int. Cl.$^5$ .................. C07D 711/42; C07D 711/46; C07C 143/76
[52] U.S. Cl. .................................... 544/158; 544/384; 544/399; 546/722; 546/790; 546/301; 546/342; 548/544; 548/547; 548/551; 548/556; 548/573; 548/271
[58] Field of Search ................ 558/271, 273; 544/109, 544/110, 337, 158, 384, 399; 548/575, 544, 547, 551, 556, 573; 546/222, 290, 342

[56] References Cited

U.S. PATENT DOCUMENTS

| | | |
|---|---|---|
| 4,686,061 | 8/1987 | Nollet et al. .......................... 558/271 |
| 4,751,015 | 6/1988 | Humphreys et al. .................. 252/99 |
| 4,788,316 | 11/1988 | Thornthwaite et al. ............. 558/268 |
| 4,818,426 | 4/1989 | Humphreys et al. .................. 252/99 |

OTHER PUBLICATIONS

Gilbert, "Sulfonation and Related Reactions", Interscience Publishers, pp. 80–81, 1965.

*Primary Examiner*—Richard L. Raymond
*Assistant Examiner*—Raymond Covington
*Attorney, Agent, or Firm*—Milton L. Honig

[57] ABSTRACT

A process is described for obtaining sulfophenyl quaternary ammonium or phosphonium substituted carbonic acid esters. These esters are prepared through sulfonation with sulfur trioxide of aromatic chloroformates followed by reaction of the sulfonated aromatic chloroformate with quaternary ammonium or phosphonium substituted alcohols. The resultant sulfophenyl esters are useful as bleach precursors in combination with peroxygen compounds such as sodium perborate or percarbonate.

21 Claims, No Drawings

SULFUR TRIOXIDE SULFONATION OF AROMATIC CHLOROFORMATES

BACKGROUND OF THE INVENTION

1. Field of the Invention

The invention relates to a process for preparing sulfonated phenyl carbonic acid esters having a quaternary group, which esters are useful as bleach precursors in detergent compositions.

2. The Prior Art

Detergent compositions that rely upon sodium perborate as a bleach normally require a precursor to activate the oxygen-releasing compound where wash-water temperatures are below 60° C. A recently issued patent, U.S. Pat. No. 4,751,015 (Humphreys et al.), reported an exceptionally effective bleach precursor family of compounds identified as quaternary ammonium or phosphonium substituted peroxy carbonic acid esters. These precursors were reported synthesized in a two-step procedure. Illustrative is 2-(N,N,N-trimethylammonium)ethyl sodium 4-sulphophenyl carbonate chloride (SPCC) which was synthesized by first preparing choline chloroformate chloride through reaction of phosgene with choline chloride in a chloroform solution. The choline chloroformate chloride was then isolated as a crystalline solid. In a second step, the solid choline chloroformate chloride was added to an aqueous solution of sodium 4-phenol sulfonate containing an equimolar amount sodium hydroxide.

A number of problems are associated with this process. For instance, there are handling difficulties with choline chloroformate chloride, a highly hygroscopic material. Spontaneous crystallization of the chloroformate from solution has been noted. This presents a challenge in commercial production to avoid pipeline constriction. Furthermore, yields of the final product, SPCC, are variable, sometimes being even quite poor (40-85%). Instability of the final product is a still further problem.

Final bleach precursor product, e.g. SPCC, resulting from this process normally contains a very substantial amount of sodium chloride. This by-product is undesirable for several reasons. Sodium chloride promotes corrosion of certain metallic parts of washing machines. Further, sodium chloride takes up valuable space within a detergent formulation without contributing any useful function.

Another synthetic route has been suggested which involves a direct sulfonation reaction. More than one equivalent of sulfonating agent (e.g. sulfur trioxide) normally is required in the sulfonation of quaternary ammonium, phosphonium or sulfonium substituted aryl esters of carbonic or carboxylic acids when the associated counterion has basic or nucleophilic properties. This requirement results from the counterion complexing quite strongly with the sulfonating agent. For instance, chloride complexes with sulfur trioxide to form $ClSO_3^-$. Similarly, the bisulfate anion and sulfate dianion complexes with sulfur trioxide forming $HS_2O_7^-$ and $S_2O_7^=$, respectively.

Problems of counterion complexing can be overcome if the ester is sulfonated with oleum, a procedure reported in co-pending U.S. patent application Ser. No. 07/272,143. Therein the actual sulfonating agent is the sulfuric acid component of oleum. On the other hand, the sulfur trioxide component acts as an internal desiccant for the water formed as a by-product of sulfuric acid sulfonation. Although good yields are readily obtained and a product free of sodium chloride (when the counterion is chloride) is formed, a sulfonated aryl ester is obtained that has significant levels of sodium sulfate. Under optimum reaction conditions the finished product contains approximately 40-45% of the desired sulfonated aryl ester, 55-60% sodium sulfate and 1% sodium chloride. Although sodium sulfate is a component of most finished fabrics washing powders, a process which results in high active ester would permit greater flexibility during the formulation of this material.

Consequently, it is an object of the present invention to provide an improved process for the synthesis of quaternary ammonium or phosphonium substituted carbonic acid esters.

A more specific object of the present invention is to provide an improved process for obtaining the aforementioned carbonic acid esters which limits the amount of sodium chloride and/or sodium sulfate present in the final product.

A further object of the present invention is provide a synthesis of carbonic acid esters that results in a high and relatively reproducible product yield.

A still further object of the present invention is to provide an improved process for obtaining the aforementioned carbonic acid esters but without the necessity of a separate neutralization step.

These and further objects of the present invention will become more evident from the detailed description that follows.

SUMMARY OF THE INVENTION

A process is provided for preparation of sulfophenyl quaternary ammonium and phosphonium carbonate esters of the formula:

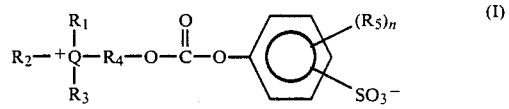

wherein:
R$_1$, R$_2$ and R$_3$ are each a radical selected from the group consisting of alkyl, alkenyl, alkynyl, cycloalkyl, cycloalkenyl, alkaryl, aryl, phenyl, hydroxyalkyl, and polyoxyalkylene;
or two or more of R$_1$, R$_2$ and R$_3$ together form an alkyl substituted or unsubstituted nitrogen-containing heterocyclic ring system;
or at least one of R$_1$, R$_2$, and R$_3$ is attached to R$_4$ to form an alkyl substituted or unsubstituted nitrogen-containing heterocyclic ring system;
R$_4$ is selected from a bridging group consisting of alkylene, cycloalkylene, alkylenephenylene, phenylene, arylene, and polyalkoxylene; and wherein the bridging group can be unsubstituted or substituted with C$_1$-C$_{20}$ atoms selected from alkyl, alkenyl, benzyl, phenyl and aryl radicals;
Q is nitrogen or phosphorous;
R$_5$ is C$_1$-C$_{12}$ alkoxy, carboxy, C$_1$-C$_{12}$ alkyl carboxy group and mixtures thereof; and
n ranges from 0 to 4;
comprising the steps of:
(i) reacting an aryl chloroformate of the formula:

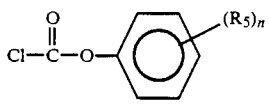

with sulfur trioxide in a molar ratio to provide effective amounts of each reactant to form an aryl sulfonated chloroformate; and (ii) condensing said aryl sulfonated chloroformate with a quaternized hydroxy compound to form the carbonate esters, said quaternized hydroxy compound having the formula:

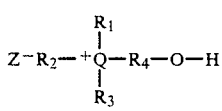

wherein Z is a mono- or multi-valent anion leading to charge neutrality when combined with $Q^+$ in the appropriate ratio.

DETAILED DESCRIPTION OF THE INVENTION

According to the present invention, an improved process has been discovered which results in a high active sulfophenyl quaternary ammonium substituted ester product. The process entails sulfonation of an aromatic chloroformate, e.g. phenyl chloroformate, with sulfur trioxide followed by reaction of the resultant sulfonated chloroformate with a quaternary ammonium, phosphonium or sulfonium substituted alcohol. If the alcohol has a halide counterion then no neutralization needs to be performed on the final reaction mixture. Schematically, the process can be represented through equations (1) and (2) for a typical reaction between phenyl chloroformate and choline chloride.

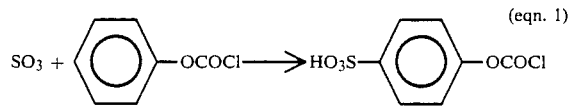

(eqn. 1)

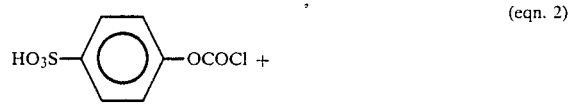

(eqn. 2)

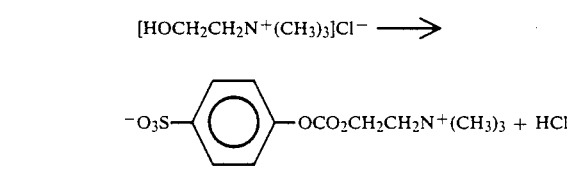

By this invention, it has been found that only one equivalent of sulfur trioxide is necessary to effect complete sulfonation. This is as a result of the chloroformate not carrying a labile chloride ion that can complex any of the sulfonating agent. It was surprising that the sulfonation of phenyl chloroformate was successful under any conditions since it is well known that sulfonation of acid chlorides with sulfur trioxide results in the sulfonyl chloride of the carboxylic acid. In fact, this latter rearrangement did occur under vigorous reaction conditions, i.e. sulfur trioxide for 3 hours at 110°–160° C. as reported in Gilbert "Sulfonation and Related Reactions", Interscience Publishers, 1965, pp. 81.

By contrast, reaction conditions for the present invention are relatively mild. Reaction temperatures ranging from $-30°$ up to $100°$ C., preferably between ambient and $70°$ C., have proven effective. Reaction times may vary, depending upon the temperature, anywhere from 1 minute up to 3 hours, preferably between about 30 minutes and 2 hours.

The product from the process of the present invention is a sulfophenyl quaternium ammonium or phosphonium carbonate ester of the formula:

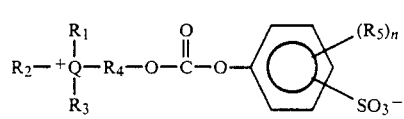

wherein:

$R_1$, $R_2$ and $R_3$ are each a radical selected from the group consisting of alkyl, alkenyl, alkynyl, cycloalkyl, cycloalkenyl, alkaryl, aryl, phenyl, hydroxyalkyl, and polyoxyalkylene;

or two or more of $R_1$, $R_2$ and $R_3$ together form an alkyl substituted or unsubstituted nitrogen-containing heterocyclic ring system;

or at least one of $R_1$, $R_2$, and $R_3$ is attached to $R_4$ to form an alkyl substituted or unsubstituted nitrogen-containing heterocyclic ring system;

$R_4$ is selected from a bridging group consisting of alkylene, cycloalkylene, alkylenephenylene, phenylene, arylene, and polyalkoxylene; and wherein the bridging group can be unsubstituted or substituted with $C_1$–$C_{20}$ atoms selected from alkyl, alkenyl, benzyl, phenyl and aryl radicals;

Q is nitrogen or phosphorous;

$R_5$ is $C_1$–$C_{12}$ alkoxy, carboxy, $C_1$–$C_{12}$ alkyl carboxy group and mixtures thereof; and n ranges from 0 to 4.

Although phosphonium groups where Q is phosphorous is within the scope of this invention, for economic reasons it is most preferred that Q be nitrogen. Furthermore, the precursor should preferably contain a quaternary ammonium carbon surrounded by $R_1$, $R_2$ and $R_3$ each the same or different and having $C_1$–$C_{20}$ atom radicals selected from the group consisting of alkyl, alkylaryl, benzyl, hydroxyalkyl, heterocyclic rings containing the quaternary nitrogen groups where $R_1$ and $R_4$ or $R_1$ and $R_2$ are joined together, and mixtures of groups thereof.

In particular, it is desirable that $R_1$ be a short-chain $C_1$–$C_4$ alkyl radical, preferably methyl, while $R_2$ and $R_3$ be a longer chain $C_7$–$C_{20}$ alkyl or alkylaryl, such as stearyl, lauryl, or benzyl group. With regard to the $R_4$ bridge between the quaternary nitrogen and carbonate groups, it is desirable that $R_4$ be a bridging group selected from $C_2$–$C_{20}$ alkylene, $C_6$–$C_{12}$ phenylene, $C_5$–$C_{20}$ cycloalkylene, and $C_8$–$C_{20}$ alkylenephenylene groups. Preferably, the alkylene groups should have two carbon atoms. Further, the bridging group can be unsubstituted or substituted with $C_1$–$C_{20}$ alkyl, alkenyl, benzyl, phenyl and aryl radicals.

Within the context of this invention, there may be compounds having the general structure (I) where $R_1$ and $R_4$ together or $R_1$ and $R_2$ together form an alkyl substituted or unsubstituted nitrogen-containing heterocyclic ring system. Representative of these systems are rings defining pyridine, morpholine, pyrrolidine, piperidine and piperazine.

More specific compounds are listed in U.S. Pat. No. 4,751,015 which is herein incorporated by reference.

The process is described generally as comprising the steps of:

(i) reacting an aryl chloroformate of the formula:

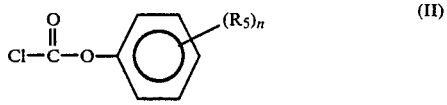

with sulfur trioxide in a molar ratio to provide effective amounts of each reactant to form an aryl sulfonated chloroformate; and (ii) condensing said aryl sulfonated chloroformate with a quaternized hydroxy compound to form the carbonate esters, said quaternized hydroxy compound having the formula:

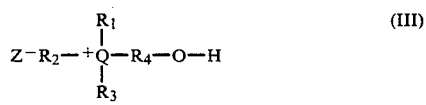

wherein Z is a mono- or multi-valent anion leading to charge neutrality when combined with Q+ in the appropriate ratio.

Solvents may be employed for the process. Suitable solvents in which the sulfonation can be performed include halocarbons such as methylene chloride and 1,2-dichloroethane; sulfur dioxide or the liquid chloroformate itself. A key advantage of the above specified solvents is that the product sulfonic acid is insoluble and readily precipitates at room temperature. This greatly facilitates the workup of the first reaction step and the precipitated product is of sufficient purity to be used in the second condensation step. Alternatively, the sulfonation can be effected in oleum alone under comparable conditions of temperature and time. However, the sulfonated chloroformate forms a pasty mass in the reaction medium and thus becomes more difficult to separate from the sulfuric acid.

Normally, the acyl chloroformate and sulfur trioxide will be present in a molar ratio anywhere from about 2000:1 to about 1:1.5, preferably between about 200:1 and about 1:1.5, optimally between about 2:1 to 1:1.

The condensation step of this process, i.e. reaction of the sulfophenylchloroformate with a positively charged alcohol, has been performed with the reactants totally solubilized, with the reactants suspended in a solvent or simply neat. The reaction step is particularly advantageous when the positively charged alcohol bears a counterion that is the conjugate base of an acid that has a pKa comparable to that of an aromatic sulfonic acid. An example of such a counterion is chloride (pKa HCl approx. −7 vs. pKa ArSO$_3$H approx. −7). When this condition is met a metathesis reaction occurs which obviates the need for neutralizing the sulfonic acid moiety of the ester product. In the case of the reaction of choline chloride and sulfophenyl chloroformate in acetonitrile the metathesis reaction results in the formation of hydrogen chloride which remains in the acetonitrile whereas the zwitterionic ester product precipitates from the solvent. In other words, both neutralization and separation are conveniently effected in one step.

In the appropriate reaction vessel the above reaction can also be performed without a solvent, i.e. choline chloride and sulfophenyl chloroformate are dry-mixed. Soon after mixing the two solids form a white viscous paste. It is believed this behavior arises from the formation of hydrogen chloride which acts to solubilize the reactants. The reaction paste is heated to 60° C. for several hours to drive both the reaction and the removal of the hydrogen chloride by-product. By the end of the heating period the paste has been transformed into a solid product with little remaining starting material and hydrogen chloride. As in the solvent based reaction neutralization is effected by the formation of hydrogen chloride but since there is no solvent its removal can be continuously carried out during the reaction period.

The following examples will more fully illustrate the embodiments of this invention. All parts, percentages and proportions referred to herein and in the appended claims are by weight unless stated otherwise.

EXAMPLE 1

Preparation of 4-Sulfophenyl Chloroformate

To a 100 mL 3-necked round bottom flask equipped with a magnetic stirrer, addition funnel topped with a drying tube containing calcium sulfate was added 35 mLs of methylene chloride. The reaction solvent was cooled with an ice water bath. To the flask was added 2.8 grams (0.035 mole) of liquid sulfur trioxide. Thereupon the reaction solution became a very pale clear yellow liquid. The ice water bath cooled reaction vessel was then charged with 5.48 grams (0.035 mole) of phenyl chloroformate added dropwise so as to control the reaction exotherm. When approximately half of the chloroformate had been added, a white precipitate began to form. Upon completion of the addition, the reaction mixture was allowed to warm to room temperature. After six hours at room temperature, a 95%+ conversion was noted by proton nmr analysis. Solvent was removed under vacuum and the remaining white to slightly off-white crystalline solid was used as is for the condensation reaction. The following spectroscopic data was obtained for this material:

PNMR (relative to external TMS); 7.5 ppm (doublet, 2H, aromatic), 7.9 ppm (doublet, 2H, aromatic), 10.3 ppm (singlet, 1H, SO$_3$H), Infrared; 1770 cm$^{-1}$ (chloroformate carbonyl), Mass spectrum; 236 m/z molecular ion.

EXAMPLE 2

Preparation of Cholyl 4-Sulfophenyl Carbonate in Acetonitrile

To a 100 mL 3-necked round bottom flask equipped with a magnetic stirrer, a reflux condenser topped with a drying tube filled with calcium sulfate were added 3.41 grams (0.0244 mole) of choline chloride and 35 mLs of acetonitrile. To this mixture was added 5.78 grams (0.0244 mole) of 4-sulfophenyl chloroformate. As soon as the chloroformate was added, a totally homogeneous solution resulted. The solution was heated to 75° C. and after 20 minutes of heating a white precipitate formed. After 24 hours, the reaction mixture was cooled to room temperature and the product was collected by filtration. HPLC analysis revealed the material to be 99–100% cholyl 4-sulfophenyl carbonate. Isolated yield was 90+%.

EXAMPLE 3

Preparation of Cholyl 4-Sulfophenyl Carbonate by Dry-Mixing

To a 100 mL 3-necked round bottom flask was added 8.28 grams (0.035 mole) of 4-sulfophenyl chloroformate and 4.87 grams (0.035 mole) of anhydrous choline chloride. The reaction flask was also equipped with a mechanical stirrer and drying tube filled with calcium sulfate. Stirring of the solids was commenced and within minutes the solid reactants became a slightly off-white paste. The paste was heated to 55°-60° C. and after two hours the paste became a solid which was impossible to mix with the attached mechanical stirrer. At this point, proton nmr indicated the material as being 75% product. The solid was physically broken into smaller fragments and heated for an additional ten hours. The white to off-white solid was analyzed by HPLC to be:

| (%) | Component |
| --- | --- |
| 91.3 | Cholyl 4-sulfophenyl carbonate |
| 2.4 | Phenolsulfonate |
| 1.4 | Choline |
| 2.3 | Chloride |
| 2.6 | Water |

The isolated yield of product was 10.9 grams (95%).

The foregoing description and examples illustrate selected embodiments of the present invention. In light thereof, various modifications will be suggested to one skilled in the art, all of which are within the spirit and purview of this invention.

What is claimed is:

1. A process for preparation of sulfophenyl quaternary ammonium and phosphonium carbonate esters of the formula:

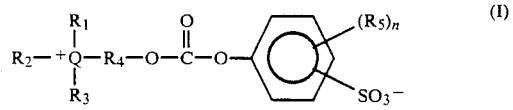

wherein:
R$_1$, R$_2$ and R$_3$ are each a radical selected from the group consisting of alkyl, alkenyl, alkynyl, cycloalkyl, cycloalkenyl, alkaryl, aryl, phenyl, hydroxyalkyl, and polyoxyalkylene;
or two or more of R$_1$, R$_2$ and R$_3$ together form an alkyl substituted or unsubstituted nitrogen-containing heterocyclic ring system;
or at least one of R$_1$, R$_2$, and R$_3$ is attached to R$_4$ to form an alkyl substituted or unsubstituted nitrogen-containing heterocyclic ring system;
R$_4$ is selected from a bridging group consisting of alkylene, cycloalkylene, alkylenephenylene, phenylene, arylene, and polyalkoxylene; and wherein the bridging group can be unsubstituted or substituted with C$_1$-C$_{20}$ atoms selected from alkyl, alkenyl, benzyl, phenyl and aryl radicals;
Q is nitrogen or phosphorous;
R$_5$ is C$_1$-C$_{12}$ alkoxy, carboxy, C$_1$-C$_{12}$ alkyl carboxy group and mixtures thereof; and
n ranges from 0 to 4;
comprising the steps of:
(i) reacting an aryl chloroformate of the formula:

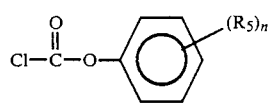

with sulfur trioxide in a molar ratio to provide effective amounts of each reactant to form an aryl sulfonated chloroformate; and
(ii) condensing said aryl sulfonated chloroformate with a quaternized hydroxy compound to form the carbonate esters, said quaternized hydroxy compound having the formula:

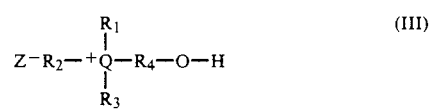

wherein Z is a mono- or multi-valent anion leading to charge neutrality when combined with Q$^+$ in the appropriate ratio.

2. A process according to claim 1 wherein the ratio of aryl chloroformate to sulfur trioxide ranges from about 2000:1 to about 1:1.5.

3. A process according to claim 1 wherein sulfonation is conducted at a temperature from about −30° up to 100° C.

4. A process according to claim 3 wherein said sulfonation requires a period of time from about 1 minute up to about 3 hours.

5. A process according to claim 1 wherein said sulfonation is conducted in a solvent selected from the group consisting of halocarbons, sulfur dioxide and liquefied chloroformate reactant.

6. A process according to claim 1 wherein said condensation of aryl sulfonated chloroformate with said quaternized hydroxy compound is conducted in the presence of a solvent.

7. A process according to claim 6 wherein said solvent is acetonitrile.

8. A process according to claim 1 wherein said condensation of aryl sulfonated chloroformate with said quaternized hydroxy compound is conducted in the absence of any additional solvent.

9. A process according to claim 1 wherein Q is nitrogen and R$_1$, R$_2$ and R$_3$ are each the same or different and selected from C$_1$-C$_{20}$ atom radicals selected from the group consisting of alkyl, alkylaryl, benzyl, hydroxyalkyl, and heterocyclic rings containing the quaternary nitrogen where R$_1$ and R$_4$ or R$_1$ and R$_2$ are joined together, and mixtures of groups therefor.

10. A process according to claim 9 wherein R$_1$ is selected from short-chain C$_1$-C$_4$ alkyl radicals.

11. A process according to claim 9 wherein R$_2$ and R$_3$ are each a longer chain C$_7$-C$_{20}$ alkyl or alkylaryl radical.

12. A process according to claim 11 wherein said longer chain radical is selected from the group consisting of benzyl, lauryl and stearyl groups.

13. A process according to claim 1 wherein R$_4$ is selected from a bridging group consisting of C$_2$-C$_{20}$ alkylene, C$_6$-C$_{12}$ phenylene, C$_5$-C$_{20}$ cycloalkylene, and C$_8$-C$_{20}$ alkylphenylene groups.

14. A process according to claim 12 wherein the R$_4$ bridging group is a C$_2$-C$_6$ alkylene or C$_6$-C$_{12}$ phenylene group.

15. A process according to claim 9 wherein said heterocyclic ring is selected from pyridine, morpholine, pyrrolidone, piperidine and piperazine.

16. A process according to claim 1 wherein the ester product is 2-(N,N,N-trimethylammonium)ethyl 4-sulfophenyl carbonate ester.

17. A process according to claim 1 wherein the ester product is 2-(N-benzyl-N,N-dimethylammonium)ethyl 4-sulfophenyl carbonate ester.

18. A process according to claim 1 wherein the ester product is 2-(N-butyl-N,N-dimethylammonium)ethyl 4-sulfophenyl carbonate ester.

19. A process according to claim 1 wherein the ester product is 2-[4-(N,N,N-trimethylammonium)phenyl]ethyl 4-sulfophenyl carbonate ester.

20. A process according to claim 1 wherein the ester product is 3-(1,1-dimethylpiperidinium) 4-sulfophenyl carbonate ester.

21. A process according to claim 1 wherein the ester product is 4-(1,1-dimethylpiperidinium) 4-sulfophenyl carbonate ester.

* * * * *